United States Patent [19]

Bastian

[11] 4,032,640

[45] June 28, 1977

[54] 4H-BENZO[4,5]CYCLOHEPTA[1,2-B]THIOPHENES

[75] Inventor: Jean-Michel Bastian, Therwil, Switzerland

[73] Assignee: Sandoz Ltd., Basel, Switzerland

[22] Filed: June 9, 1976

[21] Appl. No.: 694,152

[30] Foreign Application Priority Data

June 16, 1975 Switzerland ............ 7762/75

[52] U.S. Cl. ............ 424/263; 260/293.57; 260/294.8 B; 260/326.5 SA; 260/326.81; 260/329 F; 260/332.3 P; 260/332.5; 424/267; 424/274; 424/275

[51] Int. Cl.$^2$ ............ C07D 409/12

[58] Field of Search ............ 260/293.57, 294.8 B, 260/326.5 SA, 326.81, 329 F, 332.3 P, 332.5; 424/263, 267, 274, 275

[56] References Cited

UNITED STATES PATENTS

| | | | |
|---|---|---|---|
| 3,654,286 | 4/1972 | Bastian et al. | 260/293.57 |
| 3,682,930 | 8/1972 | Bourquin et al. | 260/293.57 |
| 3,770,728 | 11/1973 | Bourquin et al. | 260/240 TC |
| 3,853,915 | 12/1974 | Bourquin et al. | 260/332.3 P |
| 3,862,156 | 1/1975 | Bourquin et al. | 260/293.57 |
| 3,960,894 | 6/1976 | Bourquin et al. | 260/332.3 P |

Primary Examiner—G. Thomas Todd

Attorney, Agent, or Firm—Gerald D. Sharkin; Robert S. Honor; Thomas O. McGovern

[57] ABSTRACT

This invention provides new compounds of formula I,

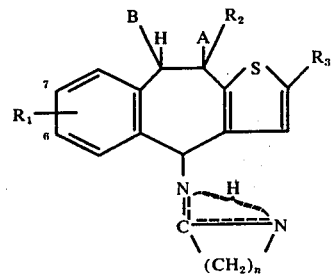

wherein.

$R_1$ is hydrogen, halogen of atomic number from 9 to 35, or alkyl or alkoxy of 1 to 4 carbon atoms, $R_2$ is hydrogen or alkyl of 1 to 4 carbon atoms, $R_3$ is hydrogen, chlorine, or alkyl of 1 to 4 carbon atoms, either A and B are each hydrogen or together a single bond, and $n$ is a whole number from 3 to 7, useful as saliaiuretics.

21 Claims, No Drawings

4H-BENZO[4,5]CYCLOHEPTA[1,2-B]THIO-PHENES

The present invention relates to benzocycloheptathiophene derivatives.

The present invention provides compounds of formula I,

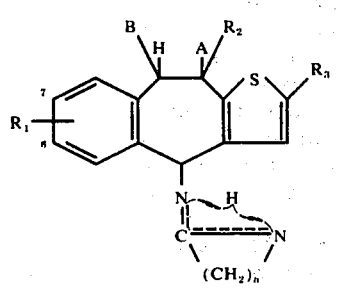

wherein
$R_1$ is hydrogen, halogen of atomic number from 9 to 35, or alkyl or alkoxy of 1 to 4 carbon atoms,
$R_2$ is hydrogen or alkyl of 1 to 4 carbon atoms,
$R_3$ is hydrogen, chlorine, or alkyl of 1 to 4 carbon atoms,
either A and B are each hydrogen or together a single bond, and
$n$ is a whole number from 3 to 7.

The compounds of formula I may exist in two tautomeric forms, e.g. of formulae Ia and Ib,

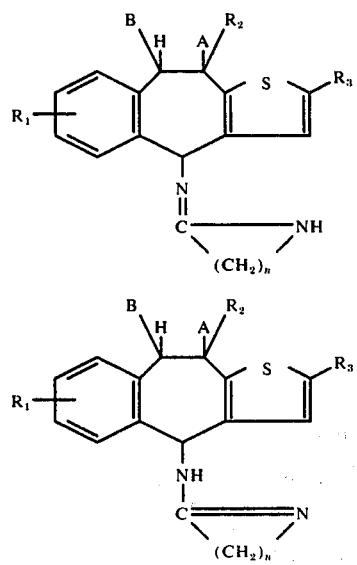

wherein $R_1$ to $R_3$, A, B and n are as defined above. For simplicity the nomenclature used herein to describe the compounds of formula I corresponds to formula Ia.

Any alkyl or alkoxy group present in a compound of formula I preferably has 1 to 2 carbon atoms, especially 1 carbon atom. $R_1$ is preferably chlorine. $R_1$ preferably is in the 6 or 7 position of the tricyclic nucleus. $R_2$ and $R_3$ preferably are hydrogen. $n$ is preferably 5.

The present invention also provides a process for the production of a compound of formula I as defined above which comprises condensing a compound of formula II,

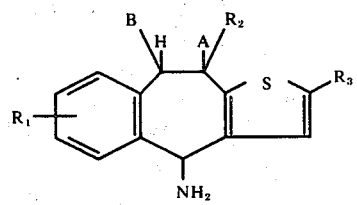

wherein $R_1$, $R_2$, $R_3$, A and B are as defined above, with a compound of formula III,

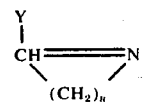

wherein
Y is chlorine, lower alkylthio or lower alkoxy, and
$n$ is as defined above.

The condensation may be effected in conventional manner for such reactions, e.g. in an inert organic solvent, preferably a polar solvent. Suitable solvents include appropriate halogenated hydrocarbons, ethers, aromatic hydrocarbons, or when Y is alkoxy or alkylthio, alternatively lower alcohols. The reaction temperature may vary from about 0° C to the reflux temperature, and is preferably room temperature.

The starting materials of formula II as defined above, may be obtained by (i) reacting a compound of formula IV,

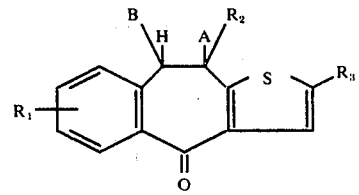

wherein $R_1$, $R_2$, $R_3$, A and B are as defined above, with hydroxylamine in conventional manner to form the corresponding oxime and (ii) reducing the oxime in conventional manner, e.g. with nascent hydrogen or complex metal hydrides.

Insofar as the production of any starting material is not particularly described these compounds are known, or may be produced and purified in accordance with known processes, or in a manner analogous to processes described herein, e.g. in the Examples, or to known processes.

Free base forms of compounds of formula I may be converted into acid addition salt forms in conventional manner and vice versa. Suitable acids for salt formation include hydrochloric acid and maleic acid.

In the following Examples all temperatures are in degrees Centigrade and are uncorrected.

EXAMPLE 1

2-(6-Chloro-9,10-dihydro-4H-benzo[4,5]cyclohepta[1,2-b]thiophene-4-ylimino)hexahydroazepine 5 ml of 98% ethanol and 10.0 g of caprolactim O-methyl ether are added to 8.0 g of 4-amino-6-chloro-9,10-dihydro-4H-benzo[4,5]cyclohepta[1,2-b]thiophene hydrochloride and are allowed to stand at room temperature while shaking occasionally. A few drops of ether are added to the resulting clear solution after 12 hours, whereupon the hydrochloride of the title compound crystallizes. M.Pt. decomp. from 185°, (recrystallized once from ethanol/ether).

The starting material may be produced as follows:

a. 80.5 g of 6-chloro-9,10-dihydro-4-hydroxyimino-4H-benzo-[4,5]cyclohepta[1,2-b]thiophene, 105 g of zinc dust and 14 g of ammonium chloride are stirred with 1750 ml of 25% ammonia solution and 350 ml of ethanol for 3 hours at the boiling temperature. Upon cooling to room temperature, the undissolved portion is filtered off and is washed with benzene. 200 ml of concentrated caustic soda solution are added to the filtrate which is extracted with a mixture of ether/benzene 1:1. The organic phase is washed with saturated common salt solution, dried over magnesium sulphate and the solvent is removed by evaporation. The remaining 4-amino-6-chloro-9,10-dihydro-4H-benzo[4,5]cyclohepta[1,2-b]thiophene is converted in ethanol into the hydrochloride. M.Pt. decomp. from 234°.

In a manner analogous to the one described in Example 1, the following compounds of formula I may be obtained by reaction of the corresponding amines of formula II produced in a manner analogous to Example 1a, with a corresponding lactim ether of formula III:

For this use the dosage will, of course, vary depending on the compound employed, mode of administration and treatment desired. However, in general, satisfactory results are obtained with a daily dosage of from about 0.1 mg to about 50 mg per kg animal body weight, conveniently given in divided doses 2 to 4 times a day or in sustained release form. For the larger mammals, the total daily dosage is in the range from about 0.1 to about 10 mg/kg animal body weight, and preferably lies in the range of from about 5 to about 100 mg, especially from about 50 to about 100 mg. Dosage forms suitable for oral administration may comprise from about 1 mg to about 50 mg, preferably from about 10 to about 50 mg of the compounds admixed with a solid or liquid pharmaceutical carrier or diluent.

In a group of compounds $R_3$ is hydrogen or alkyl.

The Example 1 compound exhibits particularly interesting activity.

The compounds of formula I may be administered in pharmaceutically acceptable acid addition salt form. Such acid addition salt forms exhibit the same order of activity as the free base forms and are readily prepared in conventional manner. The present invention also provides a phrmaceutical composition comprising a compound of formula I, in free base form or in pharmaceutically acceptable acid addition salt form, in associ-

| Ex. No. | Compound of formula I | | | | | | Physical. constants | Corresponding compound of formula II Physical. constants |
|---|---|---|---|---|---|---|---|---|
| | $R_1$ | $R_2$ | $R_3$ | A | B | n | | |
| 1A | H | H | H | H | H | 5 | M.Pt.:HCl:* 237–238° | M.Pt.: 78–80° |
| 1B | H | H | H | H | H | 4 | M.Pt.:HCl:* 247–248° | M.Pt.: 78–80° |
| 1C | H | H | H | H | H | 6 | M.Pt.:HCl:* 204–205° | M.Pt.: 78–80° |
| 1D | 7-Cl | H | H | H | H | 3 | M.Pt.:hfu:** 202–203° | M.Pt.:HCl:* 233–235° |
| 1E | 6-Cl | H | H | H | H | 4 | M.Pt.:HCl:* 259–260° | M.Pt.:HCl:* Z*** from 234° |
| 1F | 7-Cl | H | H | H | H | 5 | M.Pt.:HCl:* 184–186° | M.Pt.:HCl:* 233–235° |
| 1G | 6-Cl | H | H | H | H | 6 | M.Pt.:HCl:* 248–250° | M.Pt.:HCl:* Z*** from 234° |
| 1H | 7-Cl | H | H | H | H | 6 | M.Pt.:HCl:* 258–260° | M.Pt.:HCl:* 233–235° |
| 1I | H | H | H | Bond | | 5 | Rf: Δ 0.3 | Rf: ΔΔ 0.2 |
| 1J | H | $CH_3$ | H | Bond | | 5 | Rf: Δ 0.25 | Rf: Δ 0.6 |
| 1K | H | H | Cl | H | H | 5 | Rf: Δ 0.3 | Rf: ΔΔ 0.25 |
| 1L | H | H | $CF_3$ | H | H | 4 | Rf: Δ 0.2 | RF: Δ 0.55 |

*)HCL = Hydrochloride salt
**)hfu = Hydrogenfumarate salt
***)Z = Decomposition
Δ)Thin layer chromatogram on neutral silica gel - eluant benzene/ethanol/conc. aqueous ammonia 84:15:1
ΔΔ)Thin layer chromatogram on neutral silica gel - eluant methylene chloride In analogous manner to Example 1 the following compounds of formula I may be obtained:

| | $R_1$ | $R_2$ | $R_3$ | n | A | B |
|---|---|---|---|---|---|---|
| a) | 5-$nC_4H_9$ | $C_2H_5$ | $C_2H_5$ | 7 | H | H |
| b) | 8-$OnC_4H_9$ | $C_2H_5$ | $C_2H_5$ | 7 | H | H |

The compounds of formula I are useful as salidiuretic agents, e.g. for the treatment of edemas and in the treatment of hypertonia, as indicated in standard animal tests, for example by an increase in the excretion of water and sodium chloride in rats on p.o. administration of from about 10 to about 50 mg/kg animal body weight of the compounds in accordance with the principles of E. Fluckiger et al, Schweiz med. W'schr., 93, 1232–1237 (1967).

ation with a pharmaceutical carrier or diluent. Such compositions may be in the form of, for example, a solution, tablet or capsule.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

I claim:

1. A compound of formula I,

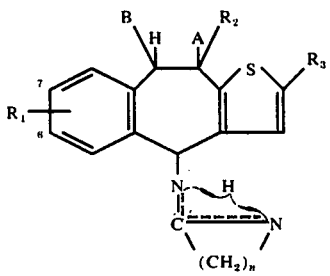

wherein
$R_1$ is hydrogen, halogen of atomic number from 9 to 35, alkyl of 1 to 4 carbon atoms, or alkoxy of 1 to 4 carbon atoms,
$R_2$ is hydrogen or alkyl of 1 to 4 carbon atoms,
$R_3$ is hydrogen, chlorine, or alkyl of 1 to 4 carbon atoms,
either A and B are each hydrogen or together a single bond, and $n$ is a whole number from 3 to 7, in the form of free base or in the form of a pharmaceutically acceptable acid addition salt thereof.

2. A pharmaceutical composition comprising a compound of claim 1 in association with a pharmaceutical carrier or diluent.

3. A method of inducing salidiuresis in animals which comprises administering a therapeutically effective amount of a compound of claim 1 to an animal in need of such treatment.

4. The compound of claim 1 which is 2-(6-Chloro-9,10-dihydro-4H-benzo[4,5]cyclohepta[1,2-b]thiophene-4-ylimino)hexahydroazepine.

5. The compound of claim 1 in which $R_1$, $R_2$, $R_3$, A, B, and $n$ are H, H, H, H, H, and 5 respectively.

6. The compound of claim 1 in which $R_1$, $R_2$, $R_3$, A, B, and $n$ are H, H, H, H, H, and 4 respectively.

7. The compound of claim 1 in which $R_1$, $R_2$, $R_3$, A, B, and $n$ are H, H, H, H, H, and 6 respectively.

8. The compound of claim 1 in which $R_1$, $R_2$, $R_3$, A, B, and $n$ are 7-Cl, H, H, H, H, and 3 respectively.

9. The compound of claim 1 in which $R_1$, $R_2$, $R_3$, A, B, and $n$ are 6-Cl, H, H, H, H, and 4 respectively.

10. The compound of claim 1 in which $R_1$, $R_2$, $R_3$, A, B, and $n$ are 7-Cl, H, H, H, H, and 5 respectively.

11. The compound of claim 1 in which $R_1$, $R_2$, $R_3$, A, B, and $n$ are 6-Cl, H, H, H, H, and 6 respectively.

12. The compound of claim 1 in which $R_1$, $R_2$, $R_3$, A, B, and $n$ are 7-Cl, H, H, H, H, and 6 respectively.

13. The compound of claim 1 in which $R_1$, $R_2$, $R_3$, and $n$ are H, H, H, and 5 respectively and A and B together is a single bond.

14. The compound of claim 1 in which $R_1$, $R_2$, $R_3$, and $n$ are H, $CH_3$, H, and 5 respectively and A and B together is a single bond.

15. The compound of claim 1 in which $R_1$, $R_2$, $R_3$, A, B, and $n$ are H, H, Cl, H, H, and 5 respectively.

16. The compound of claim 1 in which $R_1$, $R_2$, $R_3$, A, B, and $n$ are H, H $CH_3$, H, H, and 4 respectively.

17. A pharmaceutical composition according to claim 2, comprising 1 to 50 milligrams per unit dosage.

18. A pharmaceutical composition according to claim 2 in which the compound is 2-(6-Chloro-9,10-dihydro-4H-benzo [4,5]cyclohepta[1,2-b]thiophene-4-ylimino)hexahydroazepine.

19. A method according to claim 3 in which 5 to 100 milligrams of the compound are administered daily.

20. A method according to claim 3 in which 1 to 50 milligrams of the compound are administered per unit dose.

21. A method according to claim 3 in which 1 to compound is 2-(6-Chloro-9,10-dihydro-4H-benzo[4,5-]cyclohepta [1,2-b]thiophene-4-ylimino)hexahydroazepine.

* * * * *